(12) United States Patent
Kidokoro et al.

(10) Patent No.: US 7,709,028 B2
(45) Date of Patent: May 4, 2010

(54) PARTICULATE PRODUCT COMPRISING PANTETHINE

(75) Inventors: Motonori Kidokoro, Shizuoka (JP); Yasuhiro Tsutsumi, Shizuoka (JP); Mitsumasa Nada, Shizuoka (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 858 days.

(21) Appl. No.: 10/529,207

(22) PCT Filed: Sep. 29, 2003

(86) PCT No.: PCT/JP03/12408

§ 371 (c)(1),
(2), (4) Date: Mar. 25, 2005

(87) PCT Pub. No.: WO2004/028523

PCT Pub. Date: Apr. 8, 2004

(65) Prior Publication Data

US 2006/0068016 A1 Mar. 30, 2006

(30) Foreign Application Priority Data

Sep. 30, 2002 (JP) ............................. 2002-286286

(51) Int. Cl.
*A61K 9/14* (2006.01)

(52) U.S. Cl. ..................................... 424/489

(58) Field of Classification Search ................ 424/435, 424/441, 464; 514/2, 649; *A61K 9/20*
See application file for complete search history.

(56) References Cited

U.S. PATENT DOCUMENTS 4,781,915 A 11/1988 Maruya et al.

6,287,596 B1 * 9/2001 Murakami et al. .......... 424/464

FOREIGN PATENT DOCUMENTS

| EP | 0 345 787 A2 | | 12/1989 |
|---|---|---|---|
| JP | 50-88215 | | 7/1975 |
| JP | 54-122737 | | 9/1979 |
| JP | 54-126737 | | 10/1979 |
| JP | 55-38344 | | 3/1980 |
| JP | 64-79119 | | 3/1989 |
| JP | 7-233070 | | 9/1995 |
| JP | 9-143088 | | 6/1997 |
| JP | 2001-187734 | | 7/2001 |
| WO | WO 98/02185 | * | 1/1998 |
| WO | WO98/02185 | * | 1/1998 |

OTHER PUBLICATIONS

Sigma-Aldrich website for mesh-metric conversions: http://www.sigmaaldrich.com/Area_of_Interest/Research_Essentials/Chemicals/Key_Resources/Technical_Library/Particle_Size_Conversion.html.*
Machine translation for WO 98/02185 (which is published in Japanese).*
No U.S. Patent Documents (above) or NPL.*

* cited by examiner

*Primary Examiner*—Robert A Wax
*Assistant Examiner*—Jeffrey T Palenik
(74) *Attorney, Agent, or Firm*—Oblon, Spivak, McClelland, Maier & Neustadt, L.L.P.

(57) ABSTRACT

A particulate containing a pantethine, a light anhydrous silicic acid and a microcrystalline cellulose, in which the total content of the light anhydrous silicic acid the microcrystalline cellulose amounts to a quantity that yields a 0.6 or higher adsorptivity. The present pantethine-containing particulate has a good flowability and an adequate particle size providing excellent handling properties. It is free from impediments such as blocking, and has a good storage stability.

6 Claims, No Drawings

PARTICULATE PRODUCT COMPRISING PANTETHINE

FIELD OF THE INVENTION

The present invention relates to a pantethine-containing particulate.

BACKGROUND OF THE INVENTION

Pantethine is a useful medicament for: (a) prevention and treatment of a pantothenic acid deficiency; (b) replenishment of pantothenic acid to patients suffering from wasting diseases or hyperthyroidism, or to pregnant and parturient women or breast-feeding women who have an increased demand for pantothenic acid that cannot be supplied sufficiently from foods; and (c) prevention and treatment of hyperlipidemia, atonic constipation, and side effects of streptomycin and kanamycin, improvement of acute and chronic eczema, and improvement in platelet counts and hemorrhagic tendency in blood dyscrasia, when these diseases, disorders or symptoms are presumed to be attributable to a deficiency or a metabolic disorder of pantothenic acid.

Although pantethine exists as an amorphous powder at room temperature, it is supplied as a viscous liquid in the market because it cannot maintain the powdery state due to its high hygroscopicity, and The Pharmacopoeia of Japan prescribes the pantethine as 80% aqueous pantethine solution. When manufacturing a medicament in the form of a solid dosage form, it is generally desirable to supply the medicament in a powdery state and various studies have so far been done to develop a technique to powder or solidify pantethine. For example, methods known for turning liquid pantethine into powder include a method disclosed in JP-A-S50-88215 comprising freeze-drying pantethine in the presence of a small quantity of an amino acid or a saccharide having a high eutectic point such as glycine, α-alanine, lactose, mannite, or dextran, or another method disclosed in JP-A-S55-38344 comprising freezing an aqueous pantethine solution, and crushing the resultant congelation, followed by drying.

Further, in order to provide pantethine as soliddosage forms, a number of attempts have been made including encapsulation of pantethine, or mixing pantethine with a large quantity of starches or similar ingredients to obtain a pantethine-containing powder mixture.

SUMMARY OF THE INVENTION

Accordingly, an object of the present invention is to provide a pantethine-containing particulate which can be manufactured without such cumbersome and complicated processes as freezing (freeze-drying) described above. Moreover, it has a high flowability and is free from impediments such as blocking. Further, it has an adequate particle size that provides excellent handling properties. Yet further, it has a good storage stability.

Specifically, the present invention provides a particulate comprising pantethine, a light anhydrous silicic acid and a microcrystalline cellulose, wherein the total content of the light anhydrous silicic acid and the microcrystalline cellulose amounts to a quantity that has an adsorptivity of 0.6 or higher.

Also, the present invention provides a particulate comprising pantethine, a light anhydrous silicic acid and a microcrystalline cellulose, wherein the total content of the light anhydrous silicic acid and the microcrystalline cellulose ranges from about 0.7 to about 0.9 weight parts per 1 weight part of pantethine.

Further, the present invention provides a particulate substantially comprising pantethine, a light anhydrous silicic acid and a microcrystalline cellulose.

Still further, the present invention provides a solid dosage form comprising the particulate described above.

According to the present invention, a pantethine-containing particulate can be provided efficiently.

Further, according to the present invention, a pantethine-containing particulate which has a good flowability; has an adequate particle size that provides excellent handling properties; is free from impediments such as blocking; has a good storage stability can be provided.

BEST MODE FOR CARRYING OUT THE INVENTION

Whereas pantethine is available typically in the form of liquid, the pantethine-containing particulate according to the present invention may be prepared by first adding a solution containing an adequate concentration of pantethine to a light anhydrous silicic acid and a microcrystalline cellulose, then agitating the resultant mixture so as to cause the light anhydrous silicic acid and the microcrystalline cellulose to adsorb the pantethine, and then drying the mixture.

More specifically, the pantethine-containing particulate may be prepared by spraying or dripping a pantethine solution of an adequate concentration (for example, about 60-80 w/w %) onto the light anhydrous silicic acid and the microcrystalline cellulose, as it is or after suitably diluting it with water, an alcohol or a hydrous alcohol, in a granulator such as a fluidized-bed granulator, a rotary fluidized-bed granulator, or an agitating granulator, and then drying the thus treated mixture. The pantethine-containing granulated substance or particulate of the present invention may also be prepared by first dispersing a part of the light anhydrous silicic acid and/or microcrystalline cellulose in a pantethine solution of an adequate concentration or in its suitably diluted solution with water, an alcohol or an hydrous alcohol, then spraying or adding the resultant dispersion onto or to the remainder of the light anhydrous silicic acid and/or the microcrystalline cellulose in the granulator, and finally drying the same. The latter method provides more efficient preparation of the pantethine-containing particulate in that the light anhydrous silicic acid and/or microcrystalline cellulose may be added in a quantity larger than the maximum amount that can be loaded in the granulator. Since pantethine has high hygroscopicity, it is preferred to reduce the moisture content of the granulated substance thus prepared, preferably to 2.0% or below, more preferably to 1.5% or below and most preferably to 1.0% or below.

The particulate obtained may be screened through a sieve with a desired mesh size for classification into a particulate having a desired particle size (powders, fine granules, granules, etc.) According to the present invention, a particulate with an average particle size of 120 to 280 μm providing excellent handling properties can be readily obtained.

Further, according to the present invention, the light anhydrous silicic acid and the microcrystalline cellulose are contained in the particulate so that the total content of the light anhydrous silicic acid and the microcrystalline cellulose yields an adsorptivity of about 0.6 or above and more preferably from about 0.6 to about 0.7 per 1 weight part of pantethine. The adsorptivity as herein used refers to a value obtained by the following manner; define the adsorptivity of 1 as the weight content 66 mg of the light anhydrous silicic acid (Aerosil 200; produced by Nippon Aerosil Co., Ltd., Tokyo, Japan) which is required to adsorb 100 mg of pantethine as determined in the applicable test 1 described later; and divide said required weight content of light anhydrous silicic acid (66 mg) by the weight content of a substance required to adsorb 100 mg of pantethine. For example, a 181 mg weight content of microcrystalline cellulose (Avicel PH-101; produced by Asahi Kasei Corporation, Osaka, Japan) is required as shown in the below-described applicable test 1 and thus its adsorptivity is determined as 0.36 =(66 (mg)/181 (mg)). The adsorptivity based on the total content of the light anhydrous silicic acid (Aerosil 200) and the microcrystalline cellulose (Avicel PH-101) is determined as (light anhydrous silicic acid weight content)/(pantethine weight content)×1+(microcrystalline cellulose weight content)/(pantethine weight content)×0.36. Thus, it is determined as 139.64/200×1+24/200×0.36=0.74 based on the Formulation 1 to be described herein later.

The Formulation 6 shown in examples to be described later represents a particulate prepared using two ingredients, namely pantethine and light anhydrous silicic acid, and the light anhydrous silicic acid content thereof had an adsorptivity of 0.67 per 1 weight part of pantethine. The adsorptivity falls within the preferable range of adsorptivity specified by the present invention; however, the particulate of this formulation is undesirable due to its poor storage stability (cf. applicable test 3 to be described later). Meanwhile, formulations comprising three ingredients, namely pantethine, a light anhydrous silicic acid and a microcrystalline cellulose, result in desirable particulates having a preferred adsorptivity as well as an excellent storage stability.

Also, according to the present invention, the total content of the light anhydrous silicic acid and the microcrystalline cellulose ranges preferably from 0.7 to 0.9 weight parts and more preferably from 0.75 to 0.85 weight parts per 1 weight part of pantethine. In this connection, it is preferred that the adsorptivity is at least 0.6 and more preferably ranging from 0.6 to 0.7. Further, the weight ratio of light anhydrous silicic acid to microcrystalline cellulose in the total content of these two substances ranges preferably from 1 to 6 and more preferably from 2 to 4 per 1 weight part of pantethine.

Microcrystalline celluloses usable for the present invention include commercially available products such as Avicel PH-101, PH-102, PH-301, PH-302 and other Avicel series products, and Ceolus KG-801 and other Ceolus series products (both of these series are produced by Asahi Kasei Corporation, Osaka, Japan). Also, such commercially available products as Aerosil 200 and other Aerosil series products (produced by Nippon Aerosil Co., Ltd., Tokyo, Japan), and Carplex BS-304, BS-306, BS-304N, CS-500, FPS-500 and other Carplex series products (produced by Shionogi & Co. Ltd., Osaka, Japan) may be used as the light anhydrous silicic acid for the present invention.

In terms of the administration of the present particulate, the higher the pantethine content of the particulate is, the less the dosage of the pantethine-containing solid medicine can be. This is more advantageous for securing compliance requirements. Preferably, the particulate of the present invention contains at least 50 w/w %, and particularly preferably from 50 to 60 w/w % of pantethine.

Alternatively, according to the present invention, silicon compounds such as calcium silicate, hydrous silicon dioxide, hydrous amorphous silicon oxide, magnesium silicate, magnesium aluminum silicate, synthetic aluminum silicate, synthetic magnesium sodium silicate, natural aluminum silicate, heavy anhydrous silicic acid, or silicon dioxide may be used as the ingredient having an excellent pantethine adsorptivity instead of the light anhydrous silicic acid. These silicon compounds may be used to substitute for the whole or a part of the light anhydrous silicic acid. Likewise, a powdered cellulose may be used in place of the whole of a part of the microcrystalline cellulose. However, it is preferred that the particulate of the present invention substantially comprises pantethine, a light anhydrous silicic acid and a microcrystalline cellulose.

The particulate provided according to the present invention is useful for solid dosage forms and may be used as it is as dosage forms (powders, fine granules, or granules) or may be formulated as desired by using suitable formulation additives (flavoring agents, coating agents, etc.). The present particulate may be used to prepare tablets, capsules or the same kind of solid dosage forms based on any known formulation techniques.

Hereinafter, the present invention will be described in detail based on examples along with descriptions of applicable tests.

EXAMPLES

Applicable Test 1 Quantitative Measurement of Adsorbed Pantethine

Five gram of each ingredient shown in Table 1 was knead together with a pantethine solution (58%), respectively, in a mortar, and a part of the kneaded mixture was taken and subjected to shaping with a die and punch of 15 mm$\phi$ in a diameter for single-punch tableting machine for about 1 minute by compressing at a rate of 10 mm/min under a pressure (about 50 kg) just enough to homogenize the powder layer. After shaping, the upper punch was replaced with a punch of 6 mm$\phi$ in a diameter for single-punch tableting machine, which was placed on the center of the shaped body, and was compressed at a rate of 10 mm/min to pressurize the compacts. The stress exerted when the punch penetrated into the shaped body was recorded on a universal testing machine (Strograph C; by Toyo Seiki Seisaku-sho, Ltd., Tokyo, Japan). A slope $\Delta S$ of the initially rising linear portion of each stress-strain curve thus obtained was defined as the penetration strength, which was used as a measure of the plastic deformability of each pantethine-containing powder. The point where the penetration strengths underwent an abrupt change when varied quantities of the pantethine solution were added was determined as a plastic limit. Table 1 shows the thus obtained weight of each ingredient required to adsorb 100 mg of pantethine based on the plastic limit specified above.

TABLE 1

| Ingredients | Trade names | Quantity required to adsorb 100 mg pantethine (mg) |
|---|---|---|
| Light anhydrous silicic acid | Aerosil 200 | 66 |
| Microcrystalline cellulose | Avicel PH-101 | 181 |
| Microcrystalline cellulose | Avicel PH-102 | 172 |

Example 1

Preparation of Pantethine-containing Particulates

First, a binding liquid was prepared by mixing 3.333 kg of an aqueous solution containing 60 w/w % pantethine (2 kg as pantethine); 800 ml of purified water and 320 ml of a 99% dehydrated ethanol, and purified water was added to the mixture to make up a total volume of 4 l. Ingredients (light anhydrous silicic acid and microcrystalline cellulose) were charged in a fluidized bed granulator in an amount shown in Table 2, and mixed for 3 minutes at an inlet-air temperature of about 80° C., and then the binding liquid was sprayed onto the thus treated mixture to granulate it. After completing the spray, the resultant particulate was dried until its moisture content decreased to 1.0% or below (Loss on drying as measured by a Mettler moisture meter at 80° C., 1 d/30 s, 5 g).

TABLE 2

| Ingredients | Formulations (mg) | | | | | |
|---|---|---|---|---|---|---|
| | Formulation 1 | Formulation 2 | Formulation 3 | Formulation 4 | Formulation 5 | Formulation 6 |
| Aqueous pantethine solution (as pantethine) | 333 (200) | 333 (200) | 333 (200) | 333 (200) | 333 (200) | 333 (200) |
| Light anhydrous silicic acid | 139.64 | 120 | 110 | 110 | 120 | 133 |
| Microcrystalline cellulose | 24 | 43.6 | 53.6 | 23 | 80 | — |
| (Light anhydrous silicic acid + microcrystalline cellulose) vs. pantethine | 0.8182 | 0.818 | 0.818 | 0.665 | 1.0 | 0.665 |
| Light anhydrous silicic acid vs. cellulose | 5.818 | 2.75 | 2.05 | 4.78 | 1.5 | — |
| Total | 363.64 | 363.64 | 363.64 | 333 | 400 | 333 |
| Pantethine content (%) | 55 | 55 | 55 | 60 | 50 | 60 |
| Adsorptivity | 0.74 | 0.68 | 0.65 | 0.59 | 0.74 | 0.67 |

Applicable Test 2 Evaluation of Physical Properties

Each particulate prepared in the above-described Example 1 was subjected to the following tests. The results of the test are shown in Table 3.

(1) Measurement of Mean Particle Size

For each particulate prepared, a particle size distribution was obtained by using sieves having different mesh sizes and thence its average particle size (μm) was determined based on a relevant log-normal distribution.

(2) Measurement of Angles of Repose and Rupture

For each particulate prepared, the angle of repose (°) and angle of rupture (°) were measured by using a powder tester. The angle of rupture is an angle newly formed by a powder layer when a impact is applied to an accumulative layer of powder forming an angle of repose. The greater the difference (differential angle) between the angle of repose and the angle of rupture, the better flowability the powder will have.

TABLE 3

| | Formulation 1 | Formulation 2 | Formulation 3 | Formulation 4 | Formulation 5 | Formulation 6 |
|---|---|---|---|---|---|---|
| Mean particle size (μm) | 111 | 144 | 151 | 292 | 130 | 120 |
| Angle of repose (°) | 35 | 35 | 36 | 37 | 36 | 33 |
| Angle of rupture (°) | 13 | 15 | 15 | 19 | 19 | 12 |
| Differential angle (°) | 22 | 20 | 21 | 18 | 17 | 21 |
| Adsorptivity | 0.74 | 0.68 | 0.65 | 0.59 | 0.74 | 0.67 |

As clearly seen from Table 3 above, the particulates prepared in the Example 1 all had a good flowability. Above all, the particulates of the formulations 1, 2 and 3 exhibited an excellent flowability.

Applicable Test 3 Evaluation of Stability

To evaluate the pantethine-containing particulates prepared above for their stability, the pantethine content and the quantity of degradation products were measured by liquid chromatography in the particulates (formulations 1, 2 and 6) prepared in Example 1 above just after their preparation and after 1 month of their storage therefrom at 50° C. as packed in aluminum foil. The results of the test are shown in Table 4.

Operating Conditions

Detector used: An ultraviolet absorption photometer

Column: A stainless steel column about 4 mm in inside diameter and about 15 cm in length packed with octadecylsilanized silica gel for liquid chromatography (5 μm in particle diameter).

Column temperature: A constant temperature of about 40° C.

Mobile phase: pH3.5 phosphate buffer/acetonitrile mixed solution (6:1)

Flow rate: Adjusted the flow rate so that the retention time of pantethine is about 13 minutes

TABLE 4

| | Formulation 1 | | Formulation 2 | | Formulation 6 | |
|---|---|---|---|---|---|---|
| | Content (%) | Degradation products (%) | Content (%) | Degradation products (%) | Content (%) | Degradation products (%) |
| Initial content | 96.9 | 100 | 97.7 | 100 | 98.0 | 100 |
| After 1 month storage in Al pack at 50° C. | 93.9 | 256 | 97.0 | 173 | 94.2 | 265 |
| Adsorptivity | 0.74 | | 0.68 | | 0.67 | |

As is clear from Table 4, the granulated matter of the formulation 2 containing all three ingredients of pantethine, light anhydrous silicic acid and microcrystalline cellulose and having adsorptivity of 0.68 showed the most excellent stability in that the highest pantethine content remained therein after 1 month of storage at 50° C. from its preparation.

Applicable Test 4 Vibration Test

The particulate of the formulation 2 prepared in the Example 1 above was put in a fiber drum which was secured to a test stage was subjected to vibration test, in which first a vertical vibration of 2.0 G (gravitational acceleration) was applied for 200 minutes, then followed by 0.8 G horizontal vibration for 200 minutes and further 0.75 G vertical vibration for 100 minutes. After the vibration test, no blocking was observed in the particulate specimen.

Example 2

Preparation of Pantethine-containing Particulates

The particulate prepared in Example 1 was mixed with about 1 wt % of magnesium stearate per resulting tablet (pantethine content 200 mg/tablet) and the resultant mixture was compressed into tablets using a punch of 9.5 mmφ and 7.5 mmR.

What is claimed is:

1. A particulate consisting of:
   pantethine,
   a light anhydrous silicic acid and
   a microcrystalline cellulose,
   wherein
   a total content of the light anhydrous silicic acid and the microcrystalline cellulose ranges from 0.75 to 0.85 weight parts per 1 weight part of pantethine, and
   a weight ratio of light anhydrous silicic acid to microcrystalline cellulose in the total content of these two substances is in a range from about 2/1 to about 4/1.

2. The particulate according to claim 1, wherein a pantethine content is at least 50 w/w %.

3. The particulate according to claim 2, wherein the pantethine content ranges from 50 to 60 w/w %.

4. The particulate according to claim 1, wherein an average particle size ranges from 120 to 280 μm.

5. A solid dosage form comprising the particulate according to claim 1.

6. The solid dosage form according to claim 5, wherein the dosage form is selected from the group consisting of powders, fine granules, granules, tablets and capsules.

* * * * *